US006436123B1

(12) United States Patent
Magovern

(10) Patent No.: US 6,436,123 B1
(45) Date of Patent: Aug. 20, 2002

(54) SYSTEM APPARATUS AND METHOD FOR CLOSING SEVERED BONE OR TISSUE OF A PATIENT

(75) Inventor: James A. Magovern, Pittsburgh, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 0 days.

(21) Appl. No.: 09/519,241

(22) Filed: Mar. 6, 2000

Related U.S. Application Data

(63) Continuation of application No. 09/006,914, filed on Jan. 13, 1998, now Pat. No. 6,033,429.

(51) Int. Cl.$^7$ .............................................. A61B 17/03
(52) U.S. Cl. ........................ 606/216; 606/72; 606/74; 606/103
(58) Field of Search ............................. 606/53, 60, 69, 606/72, 73, 74, 103, 213, 215, 216, 232; 24/713.6, 713.7; D8/356; D11/208

(56) References Cited

U.S. PATENT DOCUMENTS

| | | | |
|---|---|---|---|
| 4,146,022 A | * | 3/1979 | Johnson et al. |
| 4,279,248 A | | 7/1981 | Gabbay |
| 4,532,926 A | | 8/1985 | O'Holia |
| 4,730,615 A | | 3/1988 | Sutherland et al. |
| 4,750,492 A | | 6/1988 | Jacobs |
| 4,802,477 A | | 2/1989 | Gabbay |
| 5,069,586 A | | 12/1991 | Casey |
| 5,139,498 A | | 8/1992 | Ley |
| 5,246,441 A | * | 9/1993 | Ross et al. ................... 606/53 |
| 5,356,412 A | | 10/1994 | Golds et al. |
| 5,366,461 A | | 11/1994 | Blasnik |
| 5,437,685 A | | 8/1995 | Blasnik |
| 5,462,542 A | | 10/1995 | Alesi, Jr. |
| 5,584,835 A | | 12/1996 | Greenfield |
| 5,720,747 A | | 2/1998 | Burke |
| 5,720,765 A | | 2/1998 | Thal |
| 5,810,826 A | | 9/1998 | Akerfeldt et al. |
| 5,814,071 A | | 9/1998 | McDevitt et al. |
| 5,814,073 A | | 9/1998 | Bonutti |
| 5,849,004 A | | 12/1998 | Bramlet |

FOREIGN PATENT DOCUMENTS

| | | |
|---|---|---|
| DE | 3146634 | 6/1983 |

OTHER PUBLICATIONS

R. Labitzke, G. Schrammt, U. Witzel, and P. Quisthout, "Sleeve–Rope Closure" of the median Sternotomy after Open Heart Operations, Thorac. Cardiovasc. Surgeon 31 (1983) 127–128. ©Georg Thieme Verlag Suttgart, New York, pp. 127–128.

* cited by examiner

*Primary Examiner*—David O. Reip
(74) *Attorney, Agent, or Firm*—Ansel M. Schwartz

(57) ABSTRACT

A system and method for closing a first side of a severed bone with a second side of a severed bone of a patient. The system includes a first anchor mechanism which is adapted to enter into the first side of the bone and a second anchor mechanism which is adapted to anchor into the second side of the bone. The second anchor mechanism is separate and remote from the first anchor mechanism. The system also includes a lash that extends through the first and second anchor mechanisms and which binds the first side of the severed bone with the second side of the severed bone. Preferably, the lash comprises a wire made of stainless steel or suture material. A method for closing a first side of a severed bone with a second side of a severed bone. The method includes the steps of anchoring a first anchor mechanism into the first side of the severed bone, anchoring a second anchor mechanism into a second side of the severed bone, extending a lash through a first opening of a housing of the first anchor mechanism in the first side, extending the lash through a second opening of a housing of the second anchor mechanism, pulling the lash until the first side and second side are contacting each other, and fixing the lash so the first side and second side maintain contact with each other.

8 Claims, 5 Drawing Sheets

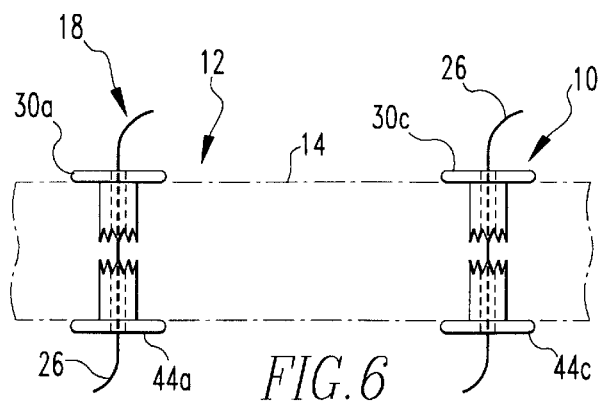
FIG. 6
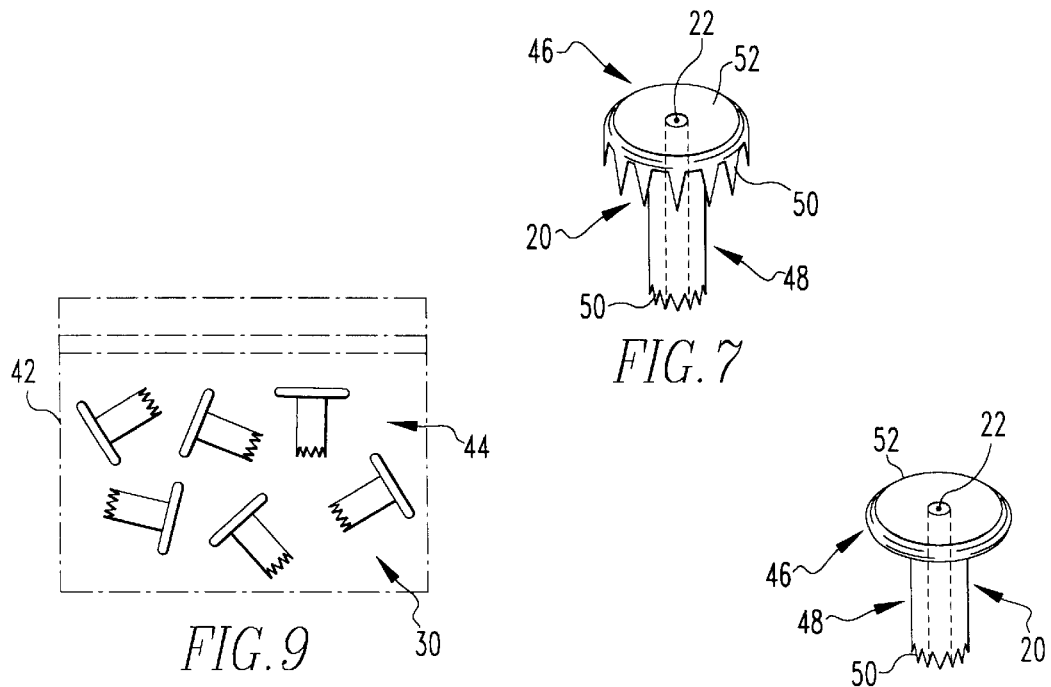
FIG. 7
FIG. 9
FIG. 8
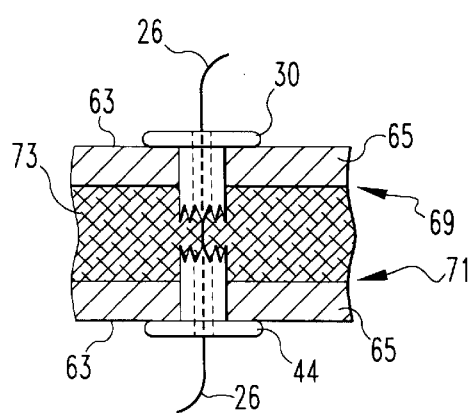
FIG. 10

SYSTEM APPARATUS AND METHOD FOR CLOSING SEVERED BONE OR TISSUE OF A PATIENT

This is a continuation application of U.S. patent application Ser. No. 09/006,914 filed Jan. 13, 1998, now U.S. Pat. No. 6,033,429.

FIELD OF THE INVENTION

The present invention is related to closing severed tissue. More specifically, the present invention is related to closing severed tissue with individualized and separate anchor mechanisms through which a wire or suture is laced to bind the severed tissue together.

BACKGROUND OF THE INVENTION

There are various circumstances in which separated tissue of a patient needs to be brought together so it can heal. Tissue is defined as bone, muscle or fascia that has been divided to gain access the thoracic cavity, mediastinum, or abdomen. For instance, in chest surgery, many times the sternum is separated so a surgeon can again gain access to the chest cavity and organs, muscle and tissue therein. After the surgeon has finished his procedure regarding the chest cavity, the sternum needs to be closed. Key to the healing process of the sternum is the proper stabilization and contact of the two severed sides together. Heretofore, there have been many techniques used to bring the separated sides of the sternum together and maintain them in contact so the healing process can occur. However, these techniques generally limit the movement the patient can experience without damaging or affecting the healing sternum.

The present invention provides for bringing the separate sides of the sternum together and maintaining them while also allowing some flexibility and movement by the patient without disturbing the healing process.

SUMMARY OF THE INVENTION

The present invention pertains to a system for closing two sides of severed tissue. The system comprises a first anchor mechanism which is adapted to enter into the first side of the tissue. The first anchor mechanism comprises a housing having a first opening which extends through the housing. The system also comprises a second anchor mechanism which is adapted to anchor into the second side of the tissue. The second mechanism comprises a housing having a second opening which extends through the housing. The second anchor mechanism is separate and remote from the first anchor mechanism. The system also comprises a lash that extends through the first opening of the first anchor mechanism and the second opening of the second anchor mechanism and which binds the first side of the severed tissue with the second side of the severed tissue when the first anchor mechanism and second anchor mechanism are anchored into the first and second sides 12, 16, respectively.

The present invention pertains to a method for closing a first side of a severed tissue with a second side of a severed tissue. The method comprises the steps of anchoring a first anchor mechanism into the first side of the severed tissue. Then there is the step of anchoring a second anchor mechanism into a second side of the severed tissue. Next there is the step of extending a lash through a first opening of a housing of the first anchor mechanism in the first side. Then there is the step of extending the lash through a second opening of a housing of the second anchor mechanism. Next there is the step of pulling the lash until the first side and second side are contacting each other. Then there is the step of fixing the lash so the first side and second side maintain contact with each other.

The present invention pertains to an anchor mechanism adapted to enter into tissue.

BRIEF DESCRIPTION OF THE DRAWINGS

In the accompanying drawings, the preferred embodiment of the invention and preferred methods of practicing the invention are illustrated in which:

FIG. 6 is a schematic representation of a cut-away side view of a first and third anchoring mechanism in tissue.

FIG. 7 is a schematic representation of a first embodiment of a grommet.

FIG. 8 is a schematic representation of an alternative embodiment of a grommet.

FIG. 9 is a schematic representation of a container having grommets.

FIG. 10 is a schematic representation of an anchoring mechanism in tissue.

DESCRIPTION OF THE PREFERRED EMBODIMENT

Figure 1:
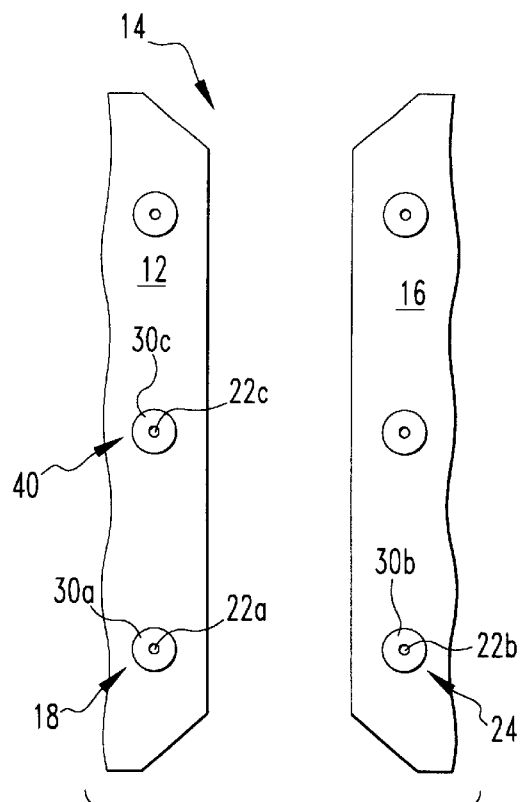
FIG. 1 is a schematic representation of a severed tissue having anchoring mechanisms of the present invention.
Figure 2:
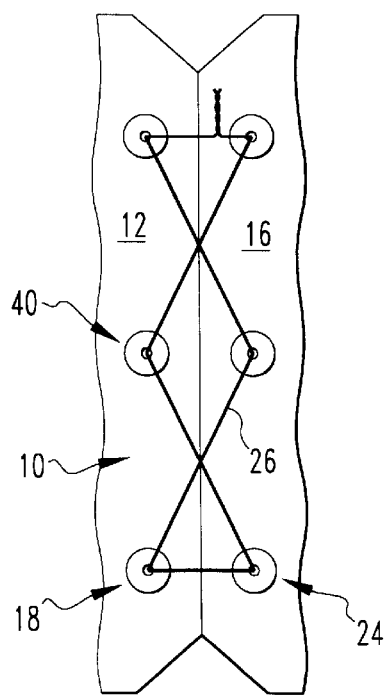
FIG. 2 is a schematic representation of a severed tissue joined together with the present invention.

Referring now to the drawings wherein like reference numerals refer to similar or identical parts throughout the several views, and more specifically to FIG. 1 thereof, there is shown a system 10 for closing a first side 12 of a severed tissue 14 with a second side 16 of the severed tissue 14 of a patient. The system 10 comprises a first anchor mechanism 18 which is adapted to enter into the first side 12 of the tissue 14. The first anchor mechanism 18 comprises a first housing 20a having a first opening 22a which extends through the first housing 20a. The system 10 also comprises a second anchor mechanism 24 which is adapted to anchor into the second side 16 of the tissue 14. The second mechanism comprises a second housing 20b having a second opening 22b which extends through the second housing 20b. The second anchor mechanism 24 is separate and remote from the first anchor mechanism 18. The system 10 also comprises a lash 26 that extends through the first opening 22a of the first anchor mechanism 18 and the second opening 22b of the second anchor mechanism 24 and which binds the first side 12 of the severed tissue 14 with the second side 16 of the severed tissue 14 when the first anchor mechanism 18 and second anchor mechanism 24 are anchored into the first and second sides, 12, 16, respectively, and the lash is tight, as shown in FIG. 2. Preferably, the lash 26 comprises a wire made of stainless steel.

Figure 3:
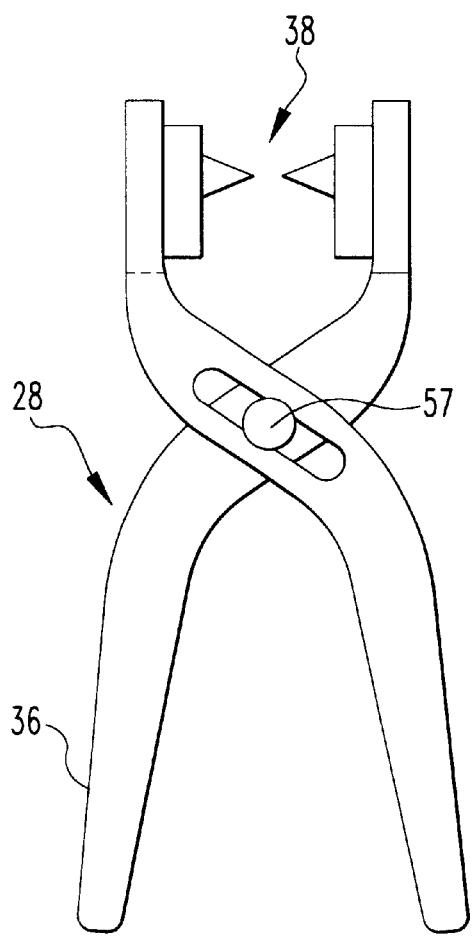
FIG. 3 is a schematic representation of an overhead view of a placing mechanism.
Figure 4:
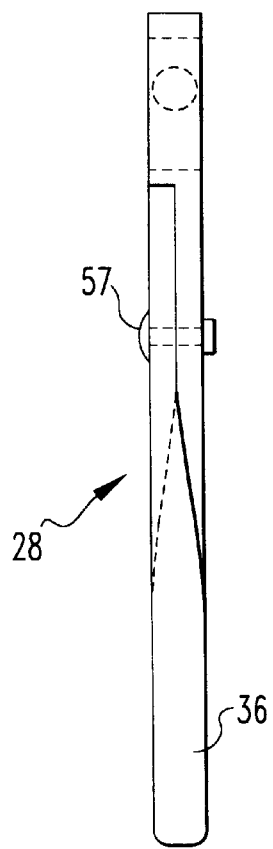
FIG. 4 is a schematic representation of a side view of a placing mechanism.
Figure 5:
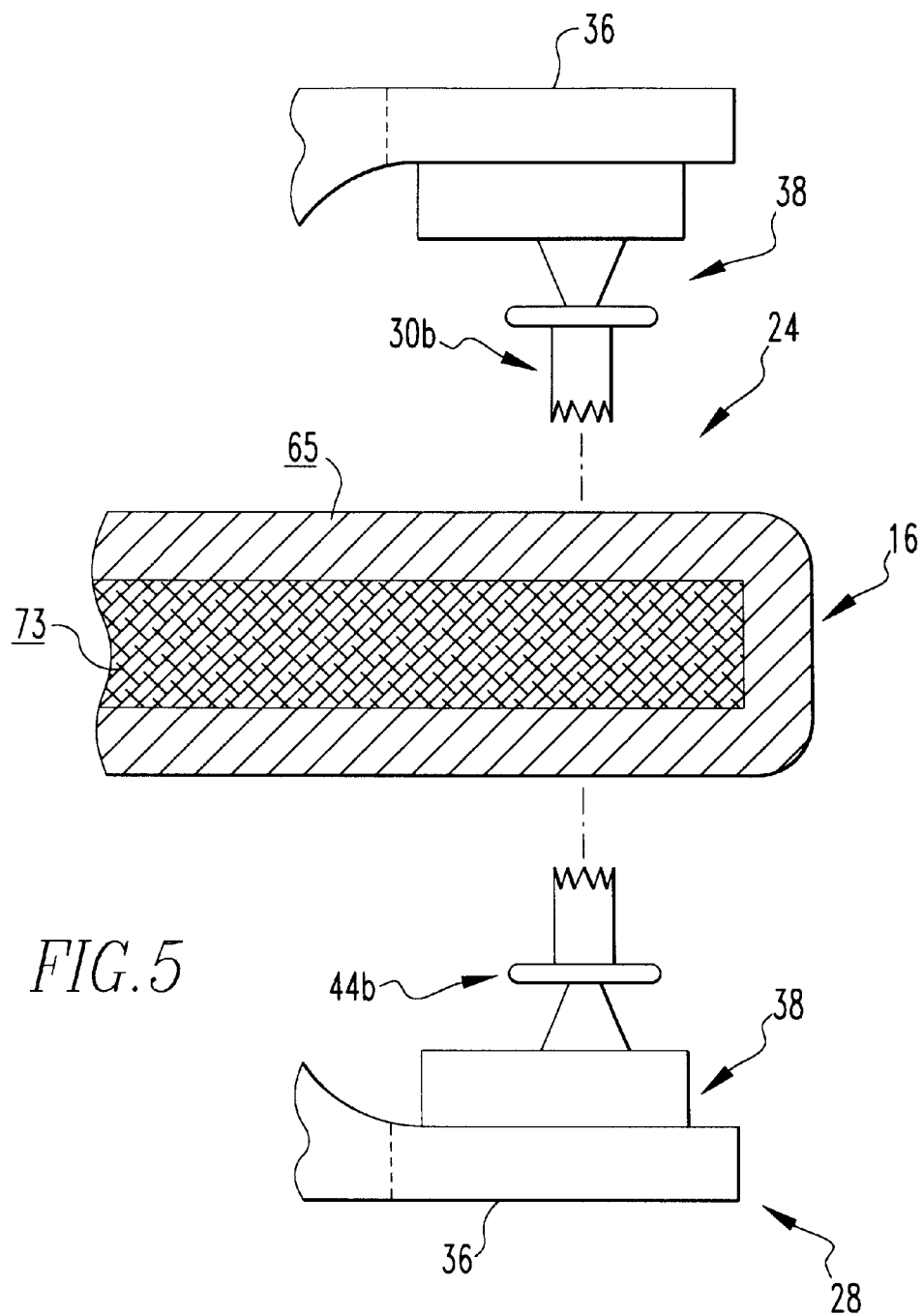
FIG. 5 is a schematic representation of a second anchoring mechanism about to be placed into tissue with the placing mechanism.
Figure 11:
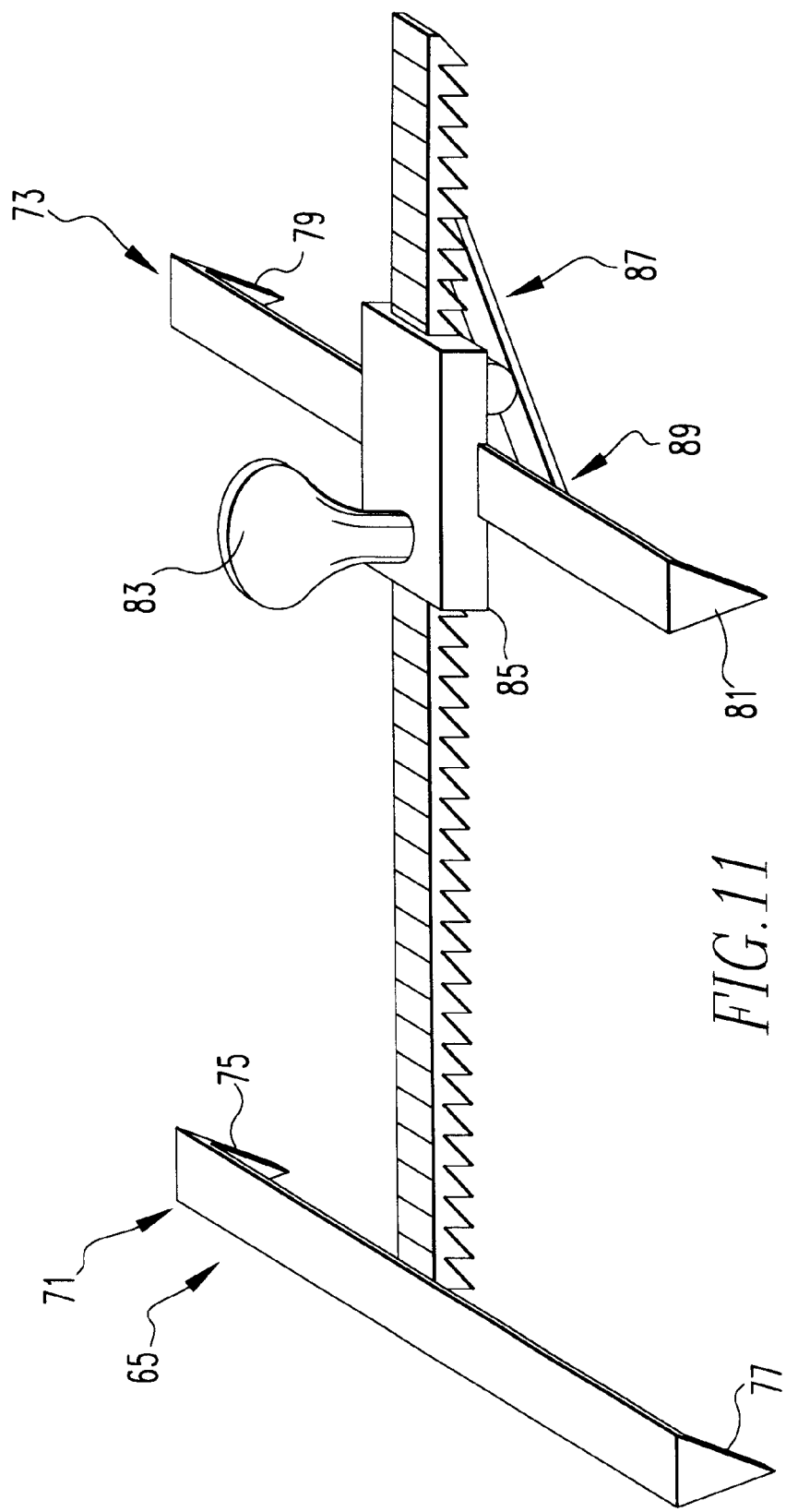
FIG. 11 is a schematic representation of a tissue approximator.

Preferably, the system 10 comprises a placement mechanism 28 for placing an anchor mechanism into tissue, as shown in FIG. 3 and FIG. 4. The placement mechanism 28 is adapted to fit about the tissue 14 and hold an anchor mechanism for placement into tissue, as shown in FIG. 5. Preferably, the first anchor mechanism 18 is a first grommet 30a and the second anchor mechanism 24 is a second grommet 30b. Preferably, the first and second anchor mechanisms 18, 24 include a first and second opposing grommet 44a, 44b, respectively. FIG. 6 shows a side view of the first grommet 30a and opposing first grommet 44a in place in tissue 14.

The placement mechanism 28 preferably comprises pliers 36, as shown in FIGS. 3 and 4, having a gripper portion 38 which is adjustable to grab the first or second side 16 of the severed tissue 14 and place a grommet 30 into the tissue 14 without damaging the tissue other than to place a grommet 30 into the tissue. Preferably, the gripper portion 38 can place an opposing grommet 44 and a grommet 30 into tissue at the same time.

Preferably, the system 10 includes a third anchor mechanism 40 having a third grommet 30c adapted to be placed in the first side 12 of the severed tissue 14, and the wire extends between and through the first, second and third grommets 30a, 30b, 30c, respectively, in a criss-cross pattern. Preferably, the wire extends through the first, second and third opposing grommets 44a, 44b, 44c after it passes through the first, second and third grommets 30a, 30b, 30c, respectively. Each grommet preferably is sterilized. The system 10 preferably includes a container .42 which holds each sterilized grommet until it is ready to be anchored to tissue.

The present invention pertains to a method for closing a first side 12 of a severed tissue 14 with a second side 16 of a severed tissue 14. The method comprises the steps of anchoring a first anchor mechanism 18 into the first side 12 of the severed tissue 14. Then there is the step of anchoring a second anchor mechanism 24 into a second side 16 of the severed tissue 14. Next there is the step of extending a lash 26 through a first opening 22a of a first housing 20a of the first anchor mechanism 18 in the first side 12. Then there is the step of extending the lash 26 through a second opening 22b of a second housing 20b of the second anchor mechanism 24. Next there is the step of pulling the lash 26 until the first side 12 and second side 16 are contacting each other. Then there is the step of fixing the lash 26 so the first side 12 and second side 16 maintain contact with each other.

Before the entering a first anchor mechanism 18 step, there are preferably the steps of putting the first anchoring mechanism onto a placement mechanism 28; and fitting the placement mechanism 28 with the first anchor mechanism 18 about the tissue. Preferably, the anchoring a first anchor mechanism 18 step includes the step of anchoring the first anchor mechanism 18 into the first side 12 of the severed tissue 14 with the placement mechanism 28. Preferably, before the putting step, there is the step of removing the first anchor mechanism 18 from a container 42 which holds the first anchor mechanism 18 which is sterilized.

The present invention pertains to an anchor mechanism adapted to enter into tissue. The anchor mechanism comprises a housing 20 having an opening 22 which extends through the housing 20. The housing 20 comprises a first portion 46 which is adapted to be disposed on the surface of the tissue, and a second portion 48 which is adapted to pierce and penetrate into the tissue.

The second portion 48 can have teeth 50 which are adapted to pierce and penetrate the tissue 14. Alternatively, and preferably, the first portion 46 is a flange 52 which extends outwardly from the second portion 48. Alternatively, the flange 52 can have teeth 50 which penetrate into tissue. Preferably, the second portion 48 extends through the tissue 14. Preferably, the cross-section of the opening 22 is circular. The cross-section of the first portion 46 and second portion 48 is preferably circular. The second portion 48 is preferably a cylinder. Preferably, the housing 20 is made of stainless steel or plastic.

In the operation of the preferred embodiment, as part of completing surgery on the patient, the sternum 14 which has been severed into a first side 12 and a second side 16, as shown in FIG. 1, needs to be closed. The surgeon or other medical technician takes pliers 36 and places a first grommet 30a on the pliers' 36 gripper portion 38 and an opposing first grommet 30a on the pliers' 36 gripper portion 38. The surgeon then places the gripper portion 38 with the first grommet 30a and opposing first grommet 30a about the first side 12 of the sternum, as shown in FIG. 5. When the surgeon is ready to enter the first grommet 30a into the first side 12 of the sternum, the surgeon squeezes the pliers 36, causing the first grommet 30a and opposing first grommet 30a to pierce the top and bottom surfaces, respectively, of the sternum and penetrate into the sternum.

Before the pliers 36 are positioned relative to the first side 12 of the sternum, the pliers 36 are adjusted so that when the pliers 36 are squeezed to plant the first grommet 30a into the first side 12 of the sternum, the gripper portion 38 of the pliers 36 will not crush or damage the bone, but allow the grommets to penetrate and enter into the first side 12 of the sternum. The pliers 36 are adjusted by rotating a screw 57 a desired amount which prevents the gripper portion 38 from closing past a certain position, as is well known in the art. See FIGS. 3 and 4. The pliers 36 have been sterilized and any grommets that are used for insertion into the sternum are provided in a sterilized plastic bag, as shown in FIG. 9, that is opened by the surgeon or medical technicians in preparation of closure of the sternum.

Each grommet has a housing 20 with an opening 22 that extends through the housing 20. The housing 20 has a flange 52 which extends outwardly from a second portion 48 of the housing 20. The second portion 48 has teeth 50, as shown in FIG. 8, which pierce and penetrate the bone whenever the pliers 36 they are placed on is squeezed and forces the second portion 48 into the bone. The grommet anchors to the bone through the second portion 48. The flange 52 catches on the respective surface of the first side 12 of the sternum and stops the grommet from penetrating too far into the first side 12 of the sternum. Alternatively, the flange 52 can have teeth 50, as shown in FIG. 7.

When the pliers 36 are squeezed with the gripper portion 38 about the first side 12 of the sternum, each grommet has its second portion 48 penetrate into the first side 12 of the sternum until the flange 52 of each grommet anchors onto the respective surface 63 of the bone layer 65 of the respective side of the first side 12 of the sternum. Since the first grommet 30a and opposing first grommet 30a are in alignment on the gripper portion 38, when they are planted with the pliers 36, the first grommet 30a and opposing first grommet 30a still align in the bone 14. A wire is then passed through the opening of the first grommet 30a and then through the opening of the opposing first grommet 30a. In this way, the wire passes through the bone layer 65 on the top 69 and bottom 71 of the first side 12 of the sternum and through cartilage 73 between the bone layers 65 of the first side 12 of the bone by passing through the first grommet 30a and opposing first grommet 30a, as shown in FIG. 10.

The wire which is then located in the housing 20 of each respective grommet does not contact the sternum but instead is protected from contacting the sternum because of the housing 20 of each grommet. When forces are created which cause the wire to be pulled laterally, instead of the possibility of the wire tearing or injuring the sternum, the respective grommets protect the sternum and specifically the surfaces of the sternum so that the sternum will not be damaged by the wire.

After the first grommet 30a and opposing first grommet 30a are in place in the first side 12 of the sternum, the process is repeated with a second grommet 30b and opposing second grommet 30b on the second side 16 of the sternum, and again repeated over and over until the desired number of grommets and opposing grommets are in place along the first side 12 and second side 16 of the sternum. Typically, eight sets of grommets and opposing grommets are placed into the separated sternum to provide protected zones for a wire to be laced in a cross-cross fashion from the first grommet 30a and opposing first grommet 30a in the first side 12 of the sternum to the second grommet 30b and the opposing second grommet 30b in the second side 16 of the sternum, and back to a third grommet 30c and opposing first grommet 30a in the first side 12 of the sternum and so on until the wire laces through the grommets and opposing grommets. The wire is then pulled by the surgeon, causing the first and second sides 12, 16 of the sternum to come together. The surgeon then ties off the wire so that the first and second sides 12, 16 of the sternum are held tightly and in contact together so they may heal and fuse together, as shown in FIG. 2, and the remaining closure of the patient is completed.

In an alternative embodiment, only one grommet is used at a time and the second portion 48 is long enough that it extends completely through the first side 12 of the sternum from the top surface of the first side 12 of the sternum to the bottom surface of the first side 12 of the sternum. The bottom of the gripper portion 38 contacts the second portion 48 as it extends out the bottom surface of the sternum. As the pliers 36 are further squeezed, the action of the bottom of the gripper portion 38 of the pliers 36 against the second portion 48 causes the teeth 50 to flare outward after the second portion 48 has pierced the bone.

Moreover, by the sets of grommets and opposing grommets being separate and apart from each other, the patient is able to move with less risk of damaging the healing bone that is fusing together by pulling it apart during movement. The separate sets of grommets act independently of each other to provide flexibility to the healing bone and allow it to-move more without causing damage to the healing process. This is because forces on any set of grommets do not necessarily cause any other set of grommets to be moved in unison and cause a shear or strain on the bone between the sets, as would happen if a bar or plate connected them. Only the forces from the wire and the immediately surrounding forces from the bone about the set of grommets effects the set of grommets and vice-versa. As is well known, bone itself is an extremely strong yet flexible material and the independent sets of grommets allows the bone to take advantage of its own properties to better allow healing to occur and not be contracted by any other objects that otherwise have been used to join severed bone 14 back together. Only the wiring itself is present to keep the separate bone together to heal.

This same technique can be applied to closure of thoracotomy or abdominal incisions. A thoracotomy is an incision that is made between the ribs to gain access to the thoracic cavity. After the operation, the ribs are re-approximated with sutures that encircle the ribs. This technique provides secure closure but can result in prolonged pain in the incision from nerve entrapment because an intercostal nerve is present on the inferior aspect of each rib. By using an anchor mechanism, it would allow the ribs to be approximated without compressing an intercostal nerve. For instance, a first grommet 30a is anchored on one side of the separated rib and a second grommet 30b is anchored on a second side of the separated rib. The wire is laced through the first and second grommets into any other grommets anchored on the separated rib. The wire is then pulled by the surgeon, causing the first and second sides of the rib to come together. The wire is then tied off and surgery is completed.

Abdominal incisions are closed with sutures which generally works quite well. However, in some patients, the sutures pull through the tissue which results in a complete wound dehiscence or the formation of an incisional hernia. The present technique provides a more secure wound closure and, reduce or eliminate the incidence of dehiscence. Grommets are placed on either side of the separated tissue. The wire is threaded through the grommets and pulled tight by the surgeon bringing the separated tissue together. The wire is then tied off.

Alternatively, a tissue approximator 65, as shown in FIG. 1, can be used to draw bone or tissue together. The tissue approximator has a first tissue grasper 71 and second tissue grasper 73 that engages the cut ends of bone or tissue with the pointed ends 75, 77, 79 and 81. A turning flange 83 for a gear mechanism 85 that moves the first and second tissue graspers towards each other, thereby approximating the divided tissue or bone. Lever arm 87 prevents the first and second tissue graspers from moving away from each other. The lever arm 87 can be disengaged by pushing the free end 89, when the tissue approximator 65 is opened or removed.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An anchor mechanism, in which a lash is disposed, adapted to enter into bone comprising:

a first grommet and a second grommet adapted to oppose the first grommet when the first grommet and the second grommet are disposed in the bone, each of which comprises:

a housing having an opening which extends through the housing through which the lash extends, said housing comprising a first portion which is adapted to be disposed on the surface of the bone, and a second portion which is adapted to pierce and penetrate into the bone, the second portion having an inner diameter which is smooth and continuous.

2. An anchor mechanism as described in claim 1 wherein the second portion has a longitudinal portion that extends from the first portion and teeth which extend from the longitudinal portion, the longitudinal portion and the teeth are adapted to pierce and penetrate the bone.

3. An anchor mechanism as described in claim 2 wherein the first portion is a flange which extends outwardly from the second portion.

4. An anchor mechanism as described in claim 3 wherein the second portion extends through the bone.

5. An anchor mechanism as described in claim 4 wherein the cross-section of the opening is circular.

6. An anchor mechanism as described in claim 5 wherein the cross-section of the first portion and inner diameter of the second portion is circular.

7. An anchor mechanism as described in claim 6 wherein the second portion is a cylinder.

8. An anchor mechanism as described in claim 7 wherein the housing is made of stainless steel or plastic or absorbable material.

* * * * *